United States Patent [19]

Kuranda

[11] Patent Number: 5,888,757
[45] Date of Patent: Mar. 30, 1999

[54] CELL WALL ASSAY

[75] Inventor: Michael Joseph Kuranda, Acton, Mass.

[73] Assignee: Millennium Pharmaceuticals, Inc., Cambridge, Mass.

[21] Appl. No.: 642,512

[22] Filed: May 3, 1996

[51] Int. Cl.$^6$ .............................. C12Q 1/48; C12Q 1/00; G01N 33/53

[52] U.S. Cl. ........................ 435/15; 435/7.2; 435/7.31; 435/7.32; 435/7.91-7.95; 435/97; 435/14; 435/4; 435/810; 435/69.2; 435/100; 435/101; 435/105; 435/183; 435/223; 435/224; 435/329; 514/1; 514/23; 514/54; 514/55; 436/89; 436/92; 436/94; 530/370; 530/371; 530/387.1; 530/387.5

[58] Field of Search .................................. 435/7.2, 7.31, 435/7.32, 7.91, 7.92, 7.93, 7.94, 7.95, 15, 97, 14, 4, 810, 69.2, 100, 101, 105, 183, 223, 224, 329; 436/89, 92, 94; 536/11, 1.11; 514/54, 55, 23, 1; 530/370, 371, 387.1, 387.5

[56] References Cited

U.S. PATENT DOCUMENTS

| | | | |
|---|---|---|---|
| 4,320,194 | 3/1982 | Bull | 435/7 |
| 4,737,453 | 4/1988 | Primus | 435/5 |
| 5,004,699 | 4/1991 | Winters | 435/7.31 |
| 5,149,632 | 9/1992 | Notermans et al. | 435/7.31 |
| 5,266,461 | 11/1993 | Tanaka | 435/7.21 |
| 5,292,648 | 3/1994 | Masubuchi et al. | |
| 5,426,026 | 6/1995 | Jordan | |
| 5,501,957 | 3/1996 | Dennis et al. | 435/15 |

OTHER PUBLICATIONS

Hector, Richard F., "A 96–Well Epifluorescence Assay for Rapid Assessment of Compounds Inhibitory to Candida ssp.", Journal of Clinical Microbiology, Oct. 1986, vol. 24, No. 4. pp. 620–624.

West, Christopher M., "Identification of Concanavalin A Receptors and Galactose–Binding Proteins in Purified Plasma Membranes of Dictyostelium Discoideum", The Journal of Cell Biology, vol. 74, 1977, pp. 264–273.

*Primary Examiner*—Paula K. Hutzell
*Assistant Examiner*—Khalid Masood
*Attorney, Agent, or Firm*—Fish & Richardson P.C.

[57] ABSTRACT

Disclosed are methods that can be used to (1) measure the level of polysaccharide in a sample; (2) measure the ability of a compound to degrade a polysaccharide; (3) measure the ability of a compound to modulate polysaccharide synthesis; and (4) identify or distinguish a polysaccharide, and hence organism, for diagnostic purposes in clinical medicine or research. The invention stems from Applicant's discovery that polysaccharides have multiple binding sites for polysaccharide binding moieties (PBM, e.g., wheat germ agglutinin (WGA)). In each method, one PBM links the polysaccharide to a substrate, and a tagged PBM is used to detect the polysaccharide. All of these methods can be carried out rapidly and quickly in the wells of a microtiter plate, thus permitting high through-put screening of samples or test compounds.

3 Claims, 3 Drawing Sheets

CELL WALL ASSAY

BACKGROUND OF THE INVENTION

The present invention relates to a quantitative assay for polysaccharides, which can be used for the rapid identification of novel antimicrobial agents.

The natural tendency of a microorganism to mutate its genome in order to achieve antibiotic resistance provides an ongoing need for the identification of new antimicrobial agents. One class of antibacterial agents acts by inhibiting synthesis of the cell wall of the targeted microorganism. Examples of antimicrobial agents that act in this manner are penicillin and nacillin, a semi-synthetic version of penicillin. The ability of a compound to interfere with the synthesis of a cell wall in vivo can be estimated in an in vitro assay of polysaccharide levels following cell wall synthesis in vitro in the presence of the compound. Because the major structural polysaccharides in the cell wall of fungi are β-glucan and chitin, compounds that interfere with the synthesis of these polymers may have utility as antifungal agents.

Many of the previously described methods for measuring polysaccharide levels in a sample involve the transfer of a radioactively labeled monosaccharide from an activated sugar donor to a specific saccharide acceptor. For example, the level of chitin synthesized in a reaction can be determined by measuring incorporation of radiolabeled GlcNAc from Uridine-Diphosphate GlcNAc into the growing chitin chain. After physical isolation of the generated chitin, one can quantitate the amount of chitin by taking into account the specific activity of the radiolabeled sugar donor.

SUMMARY OF THE INVENTION

Applicant has discovered that polysaccharides have multiple binding sites for polysaccharide binding moieties (PBM, e.g., wheat germ agglutinin (WGA)). Thus, the invention features various assays in which one PBM links the polysaccharide to a substrate, and a tagged PBM is used to detect the polysaccharide. These methods can be used to (1) measure the level of polysaccharide in a sample; (2) measure the ability of a compound to degrade a polysaccharide; (3) measure the ability of a compound to modulate polysaccharide synthesis; and (4) identify or distinguish a polysaccharide for diagnostic or non-diagnostic purposes. All of these methods can be carried out rapidly and quickly in the wells of a microtiter plate, thus permitting high through-put screening.

Accordingly, in one aspect, the invention features a method for measuring a polysaccharide in a sample. The method involves:

providing a polysaccharide binding moiety (PBM; e.g., a lectin) that is reversibly or irreversibly bound to a substrate (e.g., the surface of a well of a polystyrene microtiter plate);

binding the polysaccharide to the PBM;

binding a tagged PBM (e.g., a WGA-horse radish peroxidase conjugate) to the polysaccharide while the polysaccharide is bound to the PBM;

while the PBM is bound to the substrate, treating the sample such that any tagged PBM not bound to the polysaccharide is separated from the sample; and measuring tagged PBM in the sample as a measure of the polysaccharide in the sample.

If desired, the polysaccharide can be synthesized in the sample prior to binding the polysaccharide to the PBM. In this method, synthesis involves providing a glycosyltransferase (e.g., chitin synthase), a monosaccharide donor (e.g., UDP-GlcNAc), and a monosaccharide acceptor (e.g., a terminal GlcNAc residue of a polysaccharide); and incubating the sample such that the glycosyltransferase catalyzes the formation of a covalent bond between the monosaccharide of the monosaccharide donor and the monosaccharide acceptor, thereby forming the polysaccharide. Where the PBM is reversibly bound to the substrate, it is preferable that the polysaccharide remain bound to the substrate while practicing the invention.

In a second aspect, the invention features a method for measuring the ability of a compound (e.g., an enzyme, such as a chitinase) to degrade a polysaccharide in a sample. This method involves contacting the polysaccharide with the compound, and then measuring the level of polysaccharide in the sample, as outlined above. The ability of the compound to degrade the polysaccharide can be determined by comparing the polysaccharide level measured in the presence of the compound with the polysaccharide level measured in a second sample which lacks the compound.

The invention further features a method for measuring the ability of a compound (e.g., an enzyme or a small organic compound) to modulate synthesis of a polysaccharide. This method involves:

(a) providing a first sample which includes a glycosyltransferase (e.g., chitin synthase), a monosaccharide acceptor (e.g., a terminal GlcNAc residue) and a monosaccharide donor (e.g., UDP-GlcNAc);

(b) incubating the sample such that the glycosyltransferase catalyzes the formation of a covalent bond between the monosaccharide of the monosaccharide donor and the monosaccharide acceptor, thereby forming the polysaccharide;

(c) providing a polysaccharide binding moiety (PBM) bound to a substrate, and washing the sample to remove any unbound material;

(d) binding the polysaccharide to the PBM;

(e) while the polysaccharide is bound to the PBM, binding a tagged PBM to the polysaccharide;

(f) while the tagged PBM is bound to the polysaccharide, and while the polysaccharide is bound to the PBM, and while the PBM is bound to the substrate, treating the sample such that any tagged PBM not bound to the polysaccharide is separated from the sample;

(g) measuring tagged PBM in the sample as a measure of the polysaccharide in the sample;

(h) repeating each of steps (a) through (h) for a second sample, where the second sample includes the compound during at least steps (a) through (b); and comparing tagged PBM measured in the first sample with tagged PBM measured in the second sample as a measure of the ability of the compound to modulate synthesis of the polysaccharide.

In variations of the above methods, the invention provides methods for identifying or distinguishing organisms by identifying or distinguishing a cell wall polysaccharide of the organism in a sample. When the sample is a body fluid (or derived from a body fluid) of a patient, the invention provides methods for diagnosing a disease or infection in the patient. More generally, these methods can be used to identify or distinguish an organism in any sample (e.g., a naturally isolated sample or a culture grown in vitro). These methods for identifying or distinguishing an organism involve:

providing a sample (e.g., body fluid, such as blood, saliva, or mucous) that includes a cell wall polysaccharide of the organism;

providing a polysaccharide binding moiety (e.g., a lectin or antibody (such as a glucan-specific antibody));

binding the PBM to a substrate;

binding the polysaccharide to the PBM;

while the polysaccharide is bound to said PBM, binding a tagged PBM (e.g., a WGA-HRP conjugate) to the polysaccharide;

while the tagged PBM is bound to the polysaccharide, and while the polysaccharide is bound to the PBM, and while the PBM is bound to the substrate, treating the sample such that any tagged PBM not bound to the polysaccharide is separated from the sample; and measuring tagged PBM in the sample to identify or distinguish the organism.

By "tag" is meant a moiety whose presence can be measured, thereby providing an indirect measurement of the polysaccharide present in the sample. For example, the tag can be a polypeptide, such as an enzymatic or non-enzymatic protein (e.g., horse radish peroxidase or green fluorescent protein). An antigenic moiety (e.g., a polypeptide to which an antibody specifically binds) can also be used as a tag. Alternatively, the tag can be a fluorescent, phosphorescent, radioactive or, preferably, chemiluminescent moiety.

By "polysaccharide binding moiety (PBM)" is meant a macromolecule (e.g., a polypeptide(s)) that specifically binds a polysaccharide. If desired, the PBM can be a lectin (e.g., wheat germ agglutinin) or a monoclonal or polyclonal antibody (e.g., BG1, which specifically binds β1→3,1→4 glucans (see, e.g., Meikle et al., 1994, Plant J. 5:1–9)).

By "glucan-specific" antibody is meant a monoclonal or polyclonal antibody that specifically binds a specific glucan (e.g., (1→4)-β-glucan; (1→3),(1→4)-β-glucan; or (1→3)-β-glucan). Such antibodies can be produced by immunizing an animal with a protein (e.g., BSA) to which the glucan is conjugated.

The invention offers several advantages. In various embodiments, the invention circumvents the need for a radioactive precursor; thus, the numerous safety concerns associated with the handling and disposal of radioisotopes can be avoided with the invention. Although the invention can be practiced with a microtiter plate, the reactions of the invention can be performed on a larger or smaller scale, if desired.

The invention is broadly applicable to the direct determination of the relevant polysaccharide from a complex mixture. Natural product extracts, for example, typically contain components that can interfere with conventional assays of polysaccharides. By binding the polysaccharide to a PBM on a substrate, the invention allows a practitioner to wash away (e.g., with water or buffer) components of the sample that may be undesirable in the assay. Additionally, for detection of polysaccharides associated with an organism, a simple chemical treatment with base, for example, typically can be used to expose the polysaccharides of the cell wall, rendering them amenable to detection in the assay. Thus, the invention requires relatively little, if any, laborious polysaccharide purification. A relatively clean sample of polysaccharide can be obtained quickly, reproducibly, and simply. The invention provides a highly reproducible method for detecting, measuring, identifying, and/or distinguishing polysaccharides in numerous samples simultaneously and rapidly. Thus, the invention can be used in high through-put screening, providing a practicable method for assaying numerous samples (e.g., samples of body fluids or potential polysaccharide synthesis inhibitors) in a medical or research setting. In practice, a medical clinician or researcher could be supplied, for example, with a kit that includes a set of microtiter plates that have one or more bound PBMS, and reagents for detecting, measuring, identifying, or distinguishing the polysaccharide.

Other features and advantages of the invention will be apparent from the following description of the preferred embodiments thereof, and from the claims.

DETAILED DESCRIPTION

The drawings will first be described.

Drawings

Figure 1:
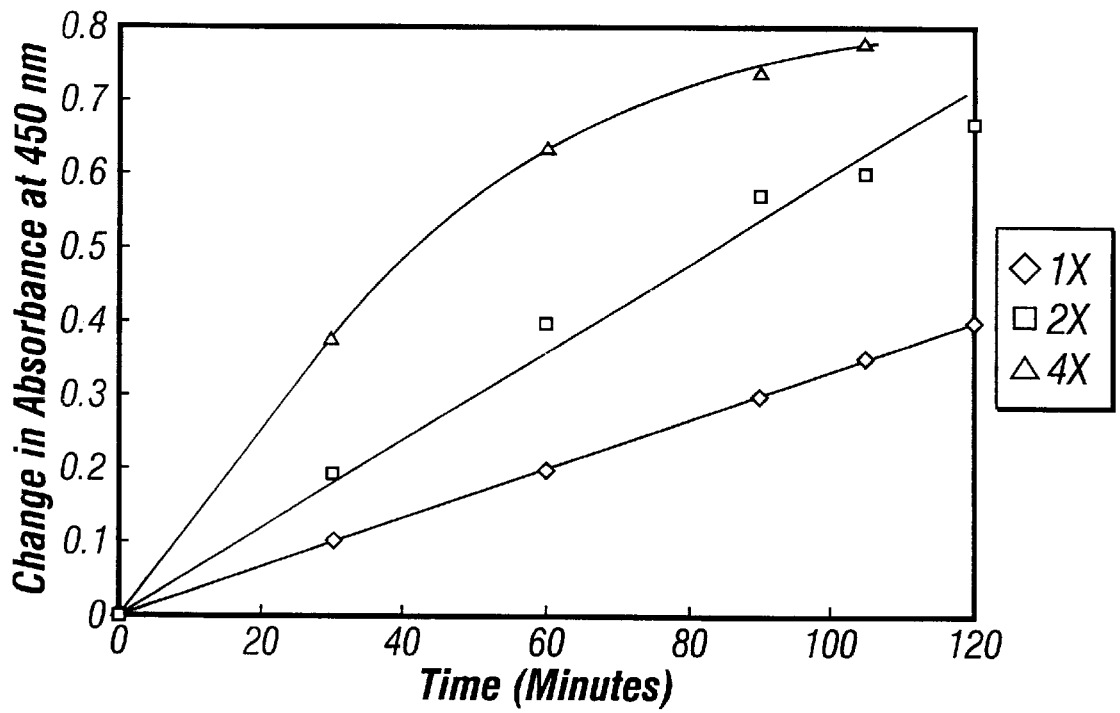
FIG. 1 is a graph illustrating trypsin activation of chitin synthase activity in membranes of recombinant yeast expressing a fungal chitin synthase. The relative signal intensity is the milliabsorbance units at 450 nm.

MEASURE OF A POLYSACCHARIDE IN A SAMPLE:

The invention provides a method for detecting and measuring a polysaccharide in a sample. In this example, chitin synthase activity was measured in vitro using chitin synthase derived from a yeast strain that was engineered to express a fungal chitin synthase in the absence of the naturally-occurring yeast chitin synthases. As is detailed below, chitin synthase derived from the engineered yeast is activated with trypsin (Caloik et al., 1971, Proc. Natl. Acad. Sci. USA 69:2052–2056). Although in this example the invention is used to measure polysaccharide that is synthesized in vitro by enzyme obtained from a genetically engineered yeast strain, the invention can also be used to measure polysaccharide that is not newly synthesized.

Preparation of CaCHS1p Membranes: In this example, chitin synthase was obtained from the S. cerevisiae strain 68-11-2C, transformed with the plasmid pJA16 (Bulawa et al., 1990, Proc. Natl. Acad. Sci. USA, 87:7424–7428 and Au-Young et al., 1990, Mol. Micro. 4:197–207). In strain 68-11-2C, the S. cerevisiae genes encoding chitin synthases 1 and 2 (CHS1 and CHS2, respectively) were genetically disrupted, rendering the strain deficient in production of these enzymes. The plasmid pJA16 encodes the chitin synthase gene of Candida albicans, and provides the only significant source of chitin in this assay.

Generally, the strain 68-1-2C/pJA16 is maintained on a supplemented SD medium. In this example, the cells were grown in 1 liter of SD medium for 48 hrs at 30° C. To provide good aeration, the culture was divided into two 500 ml cultures and grown in 2-liter flasks until the culture reached the stationary phase (i.e., until the $OD_{600}$ of the culture reached 1.2–1.4). Once harvested, the cells had a volume of approximately 4 ml, and these cells were resuspended, by vortexing, in 8 ml of 50 mM Tris-maleate, pH 6.8. The cell walls then were broken by vortexing aliquots (2 ml) of the resuspended cells for 2 minutes with 3 ml of glass beads, according to conventional protocols. The cell extracts then were centrifuged for 5 minutes at 1,000×g, and the resulting supernatant was stored at −80° C. until it was used in the chitin synthase reactions described below. Frozen CaCHS1p membranes can be thawed at 30° C. Cultures of 68-11-2C/pJA16 grown in this manner provide enough chitin synthase activity for approximately 1,500–2,000 of the assays described below.

This method for growing 68-11-2C/pJA16 is meant to be illustrative, not limiting. Of course, alternative, art-recognized methods can be used for growing the cells and preparing membranes containing chitin synthase activity. For example, chitin synthases from other fungi, bacteria, and insects can be used in the invention (see, e.g., Thomsen et al., 1995, FEMS Microbiol. Lett. 129:115–120; Mellado et al., 1995, Mol. Gen. Genet. 246:353–359; Mehmann et al., 1994, Appl. Environ. Microbiol. 60:3105–3111; Miyazaki et al., 1993, Gene 134:129–134; Cohen et al., 1993, Arch. Insect Biochem. Physiol. 22:245–261; and Das et al., 1991, Biochem. J. 280:641–647).

Figure 2:
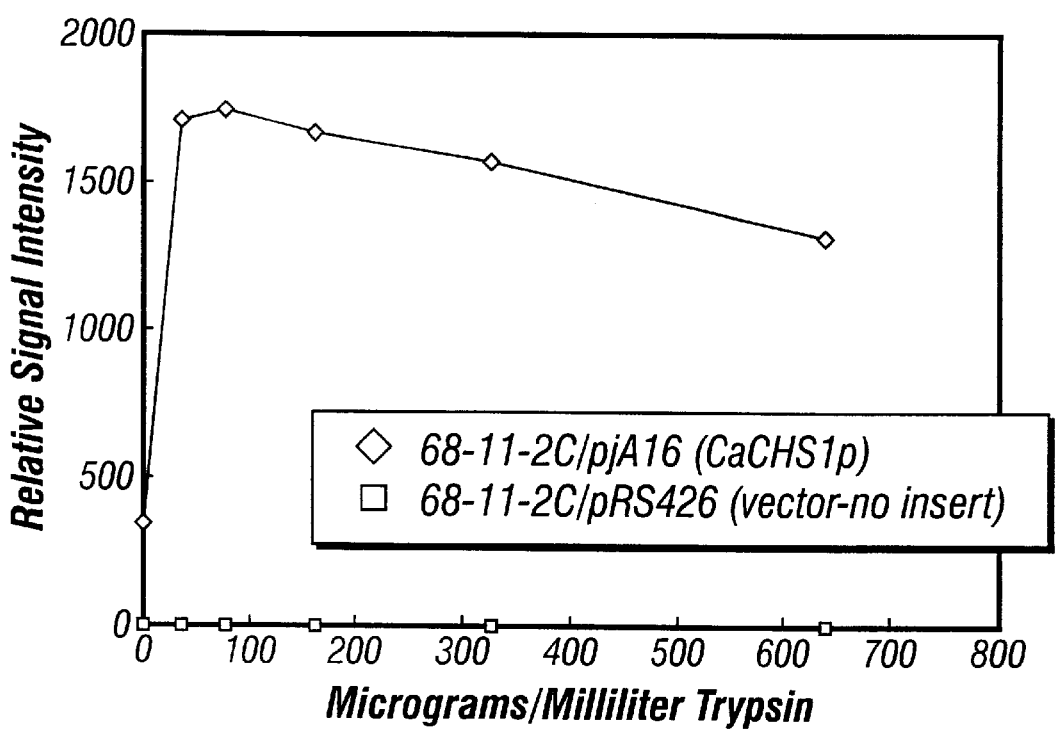
FIG. 2 is a graphic representation of the concentration and time dependence of chitin synthase activity.

Activation of CaCHS1p Membranes: Trypsin is used to activate chitin synthase in the CaCHS1p membranes. Trypsin (40 μl at 2 mg/ml) is added to a sample of prepared membranes, and the sample is incubated at 30° C. for 10 minutes. Protein hydrolysis by trypsin is stopped by the addition of trypsin inhibitor (40 μl at 3 mg/ml in 50 mM Tris-HCl, pH 7.5). As is shown in FIG. 1, a trypsin concentration of 30–500 μg/ml is suitable for activating chitin synthase. To achieve optimal sensitivity of the assay, the sample of activated CaCHS1p membranes is diluted to a concentration that provides a linear response over a 2 hour incubation period, as is illustrated in FIG. 2. Typically, a 1:4 dilution is suitable.

Preparation of Substrate Plates: In this example, the polysaccharide binding moiety (PBM) is the lectin wheat germ agglutinin (WGA), which can be bound to the surface of wells of polystyrene microtiter plates. Here, 96-well microtiter plates were coated with WGA by adding 100 μl of WGA solution (at 0.05 mg/ml) to each well, and incubating the plates and WGA for 16 hours at room temperature. Any WGA that did not bind to the plates was removed by shaking the excess solution from the plates, and then washing the plates with water 3 times. To block the free protein-binding sites on the plates, 300 μl of BSA (2 mg/ml in Tris-HCl) was incubated in each well for three hours at room temperature. The BSA blocking solution was removed by shaking the solution from the plates. A 50 μl aliquot of 2× substrate buffer containing UDP-GlcNAc (80 mM GlcNAc, 2 mM UDP-GlcNAc, 0.01M $MgCl_2$, and 0.1M Tris-maleate) then was added to each well used in the experiment. A 2× substrate buffer that lacked UDP-GlcNAc (80 mM GlcNAc, 0.01M $MgCl_2$, and 0.1M Tris-maleate) was used in the microtiter wells containing reactions used as controls. If desired, these substrate plates can be sealed (e.g., with adhesive film) and stored at −20° C. The frozen plates then are thawed for 1–2 hours at room temperature before being used in the polysaccharide assays.

Methods similar to those described above can be used to produce alternative, useful substrate plates. For example, a lectin other than WGA can be attached to the plate by incubating the plate with the lectin for 1 to 16 hours at a lectin concentration of 1 to 10 μg/ml. Preferably, the lectin is wheat germ agglutinin (*Triticum vulgaris*), *Vicia villosa*, *Phytolacca americana*, or *Lycopersicon esculentum*. Numerous lectins that are suitable for use in the assay are commercially available (e.g., from Sigma; St. Louis, Mo.). Alternatively, an antibody, such as a polyclonal or monoclonal antibody, can be used as the polysaccharide binding moiety (see, e.g., Cerenius et al., 1994, J. Biol. Chem. 269:29462–29467; Duvic et al., 1990, J. Biol. Chem. 265:9327–9332; Meikle et al., 1994, Plant J. 5:1–9; Tabata et al., 1990, Agric. Biol. Chem. 54:1953–1959; Nollstadt et al., 1994, Antimicrob. Agents Chemother. 38:2258–2265; and Biosupplies Australia Catalog No. 400-2, Parkville Victoria, Australia). Conventional techniques can be used to raise appropriate antibodies for use as PBM. Suitable antibodies also are commercially available. These antibodies, like other proteins, can be attached to substrates by incubating the proteins with the substrate. Suitable substrates include those substrates that contain a defined cross-linking chemistry (e.g., plastic substrates, such as polystyrene, styrene, or polypropylene substrates from, e.g., Corning Costar Corp., Cambridge, Mass.). If desired, a beaded particle (e.g., beaded agarose or beaded sepharose) can be used as the substrate. Conventional methods can be used to bind the PBM to such a substrate. For convenience, a practitioner can use commercially-available beads to which a PBM (e.g., a lectin, such as WGA) is already bound.

Preparation of a Tagged PBM: To detect the polysaccharide in the sample, a tagged PBM is bound to the polysaccharide while the polysaccharide is also bound to the non-tagged PBM. A subsequent washing step removes any tagged PBM that is not bound to the polysaccharide while the polysaccharide is bound to the non-tagged PBM and the non-tagged PBM is bound to the substrate. This step also washes away any undesirable components of the polysaccharide sample. The tagged PBM thus provides a measure of the polysaccharide in the sample, with the tag providing a means for detection, measuring, identifying, or distinguishing the polysaccharide.

Any tag that can be measured, or that enables the measurement of the PBM-tag conjugate, can be used in the invention. Preferably, the tag is an enzyme whose activity can be measured in vitro (e.g., horse radish peroxidase, alkaline phosphatase, β-galactosidase, or and glucose oxidase). Genes encoding all of these enzymes have been cloned, and are readily available for use by those of skill in the art. If desired, the tag can be an antigenic moiety, and such a moiety can be detected and measured with a polyclonal or monoclonal antibody and conventional methods. For example, enzymes (e.g., horse radish peroxidase, alkaline phosphatase, and β-galactosidase) can be used as antigenic moieties. Non-enzymatic proteins (e.g., serum proteins, such as bovine serum albumin and globulins; or milk proteins, such as casein) also can be used as antigenic moieties, and antibodies that specifically bind these proteins are readily available. The tag can be a moiety that can be measured by a means other than its antigenicity or enzymatic activity. For example, the polypeptide green fluorescent protein can be used as a tag and be measured under ultraviolet light. If desired, the antigenic moiety can simply be a modified form of the PBM. For example, phosphorylation of a protein often creates a new epitope that can be distinguished from the non-phosphorylated protein with the use a monoclonal antibody directed against the epitope formed by the phosphate group and protein. In a variation of this method, the tag of the tagged PBM can be a radioisotope, such as $^{125}I$ or $^{35}S$, if desired. Conventional methods for measuring radioisotopes can be used to measure PBM that is tagged with a radioisotope. In similar methods, the PBM can be tagged with a fluorescent or chemiluminescent marker (see, e.g., West and McMahon, 1977, J. Cell Biol. 74:264–273).

Methods for conjugating a measurable tag (e.g., HRP) to a PBM (e.g., a lectin such as WGA) are known in the arts of molecular biology and chemistry, and several appropriate conjugates (i.e., tagged PBM) are commercially available. For example, wheat germ agglutinin tagged with horse radish peroxidase is commercially available (see, e.g., Sigma, catalog No. L-3892).

To synthesize chitin in vitro, 20 μl of diluted CaCHS1p membranes are added to each UDP-GlcNAc-containing well of the prepared substrate plate, and the plates are incubated at room temperature for 2 hours. In this step, chitin synthase from the activated membranes uses the GlcNAc of UDP-GlcNAc to synthesize polysaccharide in vitro. To detect the polysaccharide, 100 μl of WGA-HRP solution (1 μg/ml WGA-HRP in BSA blocking solution) is added to each well, and the plates are incubated at room temperature for 15 minutes. The unbound WGA-HRP can be removed by shaking the excess WGA-HRP solution from the plate, and washing the plate with water 3 times.

The HRP tag of WGA-HRP can be detected by adding to the well an HRP substrate that forms a detectable product upon reaction with HRP. For example, reaction of HRP with OPD forms a yellow-orange product that can be measured at 490 nm. OPD is present at a concentration of at least 5 to 1 signal to noise ratio. Other measurable, art-known substrates of HRP can also be used in the invention. For convenience, commercially-prepared substrates, such as the 1-STEP TURBO TMB™ substrate (3,3',5,5' tetramethyl benzidine; 100 μL; Pierce), can be used. Once the substrate is added to each well, the plates are incubated for 10 minutes at room temperature before the reaction is stopped by the addition of 100 μl of 1M $H_2SO_4$ added to each well. Reaction of HRP with the 1-STEP TURBO TMB™ (3,3',5,5' tetramethyl benzidine) substrate produces a chromophore that can be measured by measuring the absorbance of the sample at 450 nm (e.g., using a Termo$_{max}$ Microplate Reader (Molecular Devices)). The background level of absorbance for each plate is the average of the absorbance value obtained from wells that lacked UDP-GlcNAc.

ASSAY OF THE ABILITY OF A COMPOUND TO MODULATE POLYSACCHARIDE SYNTHESIS:

The invention can be used to identify a compound that modulates (i.e., inhibits or enhances) polysaccharide synthesis. Thus, the invention provides a means for screening antifungal or antibacterial agents, for example. In this method, the compound to be tested is added to a substrate to which the preferred PBM (e.g., WGA) is bound. In vitro polysaccharide synthesis is measured in the presence of the test compound. Any compound can be tested in this assay, and fungal extracts are a preferred source of compounds to be tested. If desired, the compound (or extract containing the compound) can be dissolved in a solvent that is not expected to interfere with the chitin synthesis reaction. Examples of preferred solvents are, without limitation, water, 30% methanol, 30% dimethyl sulfoxide (DMSO), and 15% methanol/15% DMSO. Any of the preferred solvents, substituted for the compound to be tested, provides a suitable control reaction. In analyzing the absorbance data, the average background absorbance (from reactions that lacked UDP-GlcNAc) is subtracted from each of the remaining wells. The average absorbance level measured from UDP-containing wells that lacked test compounds is considered the control absorbance. The absorbance level from each test well is expressed as a fraction of the control absorbance.

EXAMPLE I

Figure 3:
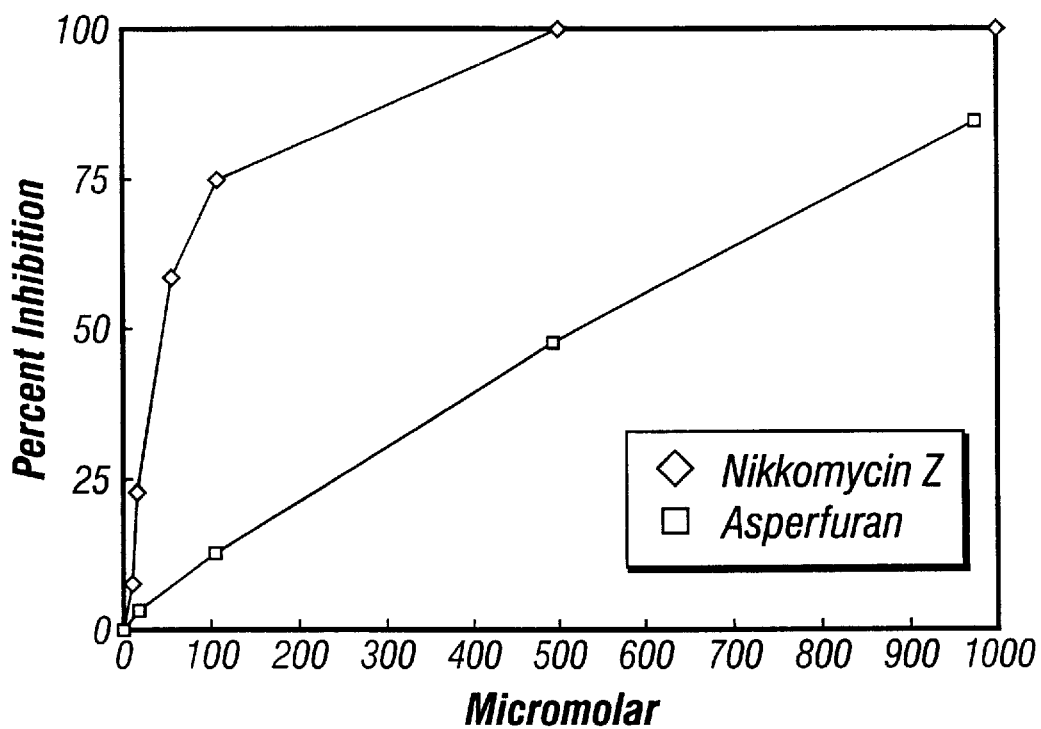
FIG. 3 is a graphic representation of the ability of the invention to measure inhibition of chitin synthase activity.

In this example, the ability of the invention to measure inhibition of polysaccharide synthesis was demonstrated with two known inhibitors of chitin synthase activity. The inhibitors, Nikkomycin Z and Asperfuran, were added to the chitin synthase reactions over a range of concentrations, to a maximal concentration of 1 mM. As is illustrated in FIG. 3, an increase in the concentration of either of these chitin synthase inhibitors causes an increase in the inhibition of chitin synthase. These data reveal that the assay provides an accurate measure of the relative potency of inhibitors, as Nikkomycin Z is known to be a more potent inhibitor of CaCHS1p activity than is Asperfuran.

EXAMPLE II

Figure 4:
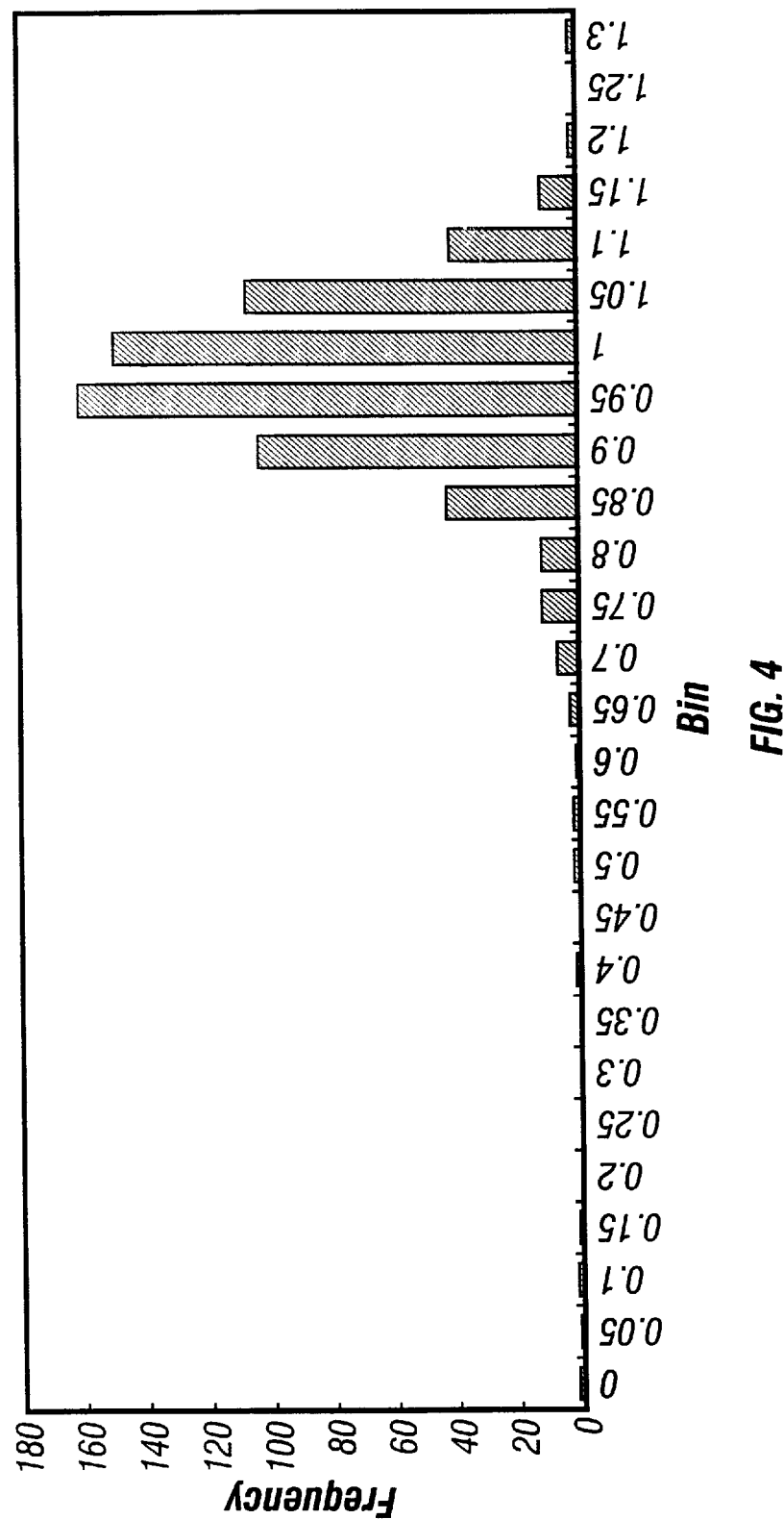
FIG. 4 is a graphic representation of the distribution of data obtained in a screen of 672 fungal extracts for chitin synthase I inhibition.

In another example, the invention was used to screen 2,000 fungal extracts for compounds that inhibit chitin synthase. FIG. 4 is a histogram showing the distribution of data from a representative screen of 672 fungal extracts. The fungal extracts were prepared by whole broth butanol extraction. The fungi tested in this screen included Guignardia, *Anthrocophyllum lateritium*, *Clavicorona pyxidata*, Arthrinium, Aspergillus (including A. niger), Cladosporium, Colletotrichum, Fusarium, Lasiodiplodia, Leptographium, Nigrospora, Penicillium, Phoma, Phomopis, Basidiodendron (*B. cinereum*, and *B. eyrei*), *Dacrymyces stillatus*, Exidia (including *E. glandulosa* and *E. populina*), Helicogloea, and Tremella (*T. fuciformis, T. globospora*, and *T. mesenterica*). As is illustrated in FIG. 4, 30% of the fungal extracts led to a reduction in the level of polysaccharide in the sample, indicating that these extracts contain a compound(s) that inhibits polysaccharide synthesis. of 2,000 extracts analyzed thus far, 12 extracts were identified that inhibited at least 70% of polysaccharide synthesis. Of these 12 extracts, 7 were re-tested for the presence of a polysaccharide synthesis inhibitory compound (s), and 4 of those extracts inhibited polysaccharide synthesis. Where a mixture of components (e.g., an impure fungal extract) is tested for the presence of a polysaccharide synthase inhibitor, conventional methods and criteria can be used to purify the inhibitor from the mixture, if desired.

ASSAY OF THE ABILITY OF A COMPOUND TO DEGRADE A POLYSACCHARIDE:

The invention also provides a method for identifying a compound(s) (e.g., an enzyme) that degrades a polysaccharide. Such a compound can be used, for example, to inhibit the growth of an organism (e.g., a fungus, bacterium, or insect) expressing the polysaccharide (e.g., chitin or glucan). In this variation of the invention, a given amount of polysaccharide is incubated with a compound, and the polysaccharide level obtained after incubation with the compound is compared with the polysaccharide level obtained in the absence of the test compound. A decrease in the level of polysaccharide after incubation with the compound indicates that the compound is a degradative enzyme (e.g., a chitinase or glucanase).

As in the other methods of the invention, the polysaccharide in this method is detected by first binding the polysaccharide to a PBM that is bound to a substrate. A tagged PBM then is added to the polysaccharide sample, and the tag is used as a measure of the level of polysaccharide in the sample. Any detectable amount of polysaccharide can be used in this method, and the optimal amount of polysaccharide may vary with the type of tag employed in the tagged PBM. Any compound can be tested for its ability to degrade a polysaccharide. Fungal and bacterial extracts are preferred sources of compounds to be tested. It is not necessary that the compound be tested, or subsequently used, in a purified form. For example, a fungal extract containing a variety of components can be tested for the presence of a polysaccharide degradative enzyme. If desired, the compound(s) responsible for degradation of the polysaccharide can subsequently be purified from the extract. Because the ability of a compound to act as a degradative enzyme varies from compound to compound, the optimal amount of compound to be used in this method will vary from compound to compound. Accordingly, it is recommended that the compound (e.g., fungal extract) be tested at more than one concentration to increase the likelihood that the degradative enzyme is detected. While the volume of the test compound is not critical, it is preferred that the volume of the entire reaction be less than 100 μl so that, for convenience, the reaction can be performed in a well of a conventional microtiter plate.

DIAGNOSTIC APPLICATIONS:

The invention also provides diagnostic methods, in which various organisms (e.g., fungi) are identified or distinguished based on the characteristics of the organism's polysaccharides. These methods can be used in a medical clinic to diagnose an infection with a pathogen (e.g., a fungus). For example, the simple detection of chitin in a body fluid of a patient indicates that the patient has a fungal infection, because chitin is specific to fungi. Diagnosis can also involve identifying or distinguishing polysaccharides in a body fluid (e.g., blood, saliva, or mucous) of a patient. These methods can also be used to identify or distinguish polysaccharides, and hence organisms (e.g., fungi), in samples other than body fluids. For example, an unidentified organism grown in vitro, or isolated from nature, can be identified or distinguished from other organisms by measuring the level of polysaccharide, or by characterizing the polysaccharide, with these methods. Such methods can be used by researchers seeking to characterize organisms (e.g., fungi).

In practicing the invention, a sample (e.g., a body fluid or a culture) is treated (e.g., with base, e.g., 1M NaOH) to disrupt fungal cells in the sample. The sample then is brought to neutral pH (e.g., with NaOAc), and the polysaccharide of the sample is bound to a PBM attached to a substrate as is decribed above. With conventional methods, it is often difficult to separate the polysaccharide from the other components of the fungal cultures. In contrast, this invention provides a simple and fast method for isolating the polysaccharide. Here, the sample is treated with base, the polysaccharide is captured by the PBM on a substrate, and the remainder of the fungal sample is washed away, thus providing a clean sample of polysaccharide.

Various organisms (e.g., species of fungi) can be identified or distinguished on the basis of the level of chitin in the sample (see, e.g., Lehmann et al., 1975, Infect. Immun. 12:987–992). In addition, because many linkages in polysaccharides (e.g., β1→3) are species-specific, various organisms can be identified or distinguished on the basis of these linkages, which can be identified or distinguished by using a glucan-specific monoclonal or polyclonal antibody as the PBM. Several such glucan-specific antibodies have been described, and conventional techniques can be used to prepare additional, preferred antibodies (see, e.g., Nollstadt et al., Tabata et al., and Meikle et al., supra).

In practicing the invention, several of these types of assays can readily be performed in parallel for any given sample. For example, the sample can be assayed in a microtiter plate that contains, in separate wells (or if desired, in the same well), monoclonal antibodies that are specific for various linkages, with the level of polysaccharide being measured generally in yet another well. All of these methods for identifying or distinguishing organisms can also be used in conjunction with conventional methods for identifying or distinguishing various organisms for medical or research purposes (e.g., identification of characteristic proteins or sequencing of the fungal DNA). Thus, conventional diagnostic methods can augment the present methods.

What is claimed is:

1. A method of screening for antifungal compounds by measuring the ability of a compound to inhibit synthesis of a polysaccharide by chitin synthase 1 said method comprising:

(a) providing a first sample comprising *C. albicans* chitin synthase 1, a monosaccharide donor, and a monosaccharide acceptor;

(b) incubating said sample such that said chitin synthase 1 catalyzes the formation of a covalent bond between the monosaccharide of said monosaccharide donor and said monosaccharide acceptor, thereby forming said polysaccharide;

(c) providing a polysaccharide binding moiety (PBM) bound to a substrate;

(d) binding said polysaccharide to said PBM;

(e) while said polysaccharide is bound to said PBM, binding a tagged PBM to said polysaccharide;

(f) while said tagged PBM is bound to said polysaccharide, and while said polysaccharide is bound to said PBM, and while said PBM is bound to said substrate, treating said sample such that any tagged PBM not bound to said polysaccharide is separated from said sample;

(g) measuring tagged PBM in said sample as a measure of said polysaccharide in said sample;

(h) repeating each of steps (a) through (h) for a second sample, wherein said second sample further comprises said compound, said compound being present at least during steps (a) through (b); and comparing the level of tagged PBM measured in said first sample with the level of tagged PBM measured in said second sample, wherein a decreased level of tagged PBM in the second sample, relative to the first sample, indicates that the compound is an antifungal agent.

2. The method of claim 1, wherein said PBM is selected from the group consisting of a lectin, a polyclonal antibody, and a monoclonal antibody.

3. The method of claim 1, wherein the tag of said tagged PBM is selected from the group consisting of a protein, a fluorescent marker, a phosphorescent marker, and a chemiluminescent marker.

* * * * *